Figure 1:
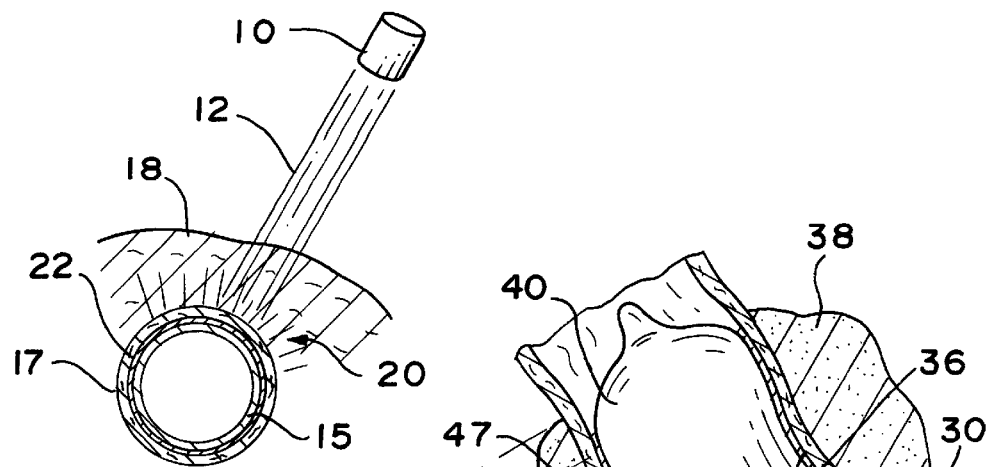

United States Patent

Regulla et al.

[11] Patent Number: 6,001,054
[45] Date of Patent: Dec. 14, 1999

[54] METHOD AND APPARATUS FOR DIFFERENTIAL ENERGY APPLICATION FOR LOCAL DOSE ENHANCEMENT OF IONIZING RADIATION

[76] Inventors: D. F. Regulla, Behamstrasse 17, 80687 Munich; Eckhard Alt, Eichendorffstrasse 52, 85521 Ottobrunn, both of Germany

[21] Appl. No.: 09/081,954

[22] Filed: May 19, 1998

[51] Int. Cl.⁶ .................................................. A61N 5/00
[52] U.S. Cl. .................................................. 600/1; 378/65
[58] Field of Search ...................... 600/1–8; 128/897–98; 378/65

*Primary Examiner*—John P. Lacyk

[57] ABSTRACT

A method for treating a site in a human body to inhibit abnormal proliferation of tissue at the site includes introducing into the body at the site a metal surface which generally conforms in shape to the shape of tissue to be treated at the site. Tissue at the site is then irradiated with ionizing radiation directed onto the metal surface from a point external to the surface so as to obtain locally enhanced radiation therapy by an amplification of the radiation dosage delivered to tissue adjacent to the metal surface as a result of backscattered radiation from the metal surface. Irradiating the tissue is performed by directing a beam of radiation with an energy content selected to have a value in a range from about 10 KeV to about 400 KeV, preferably about 40 KeV, from a point external to the body toward the metal surface and onto the tissue to be treated. The metal surface, which may be solid or composed of spaced apart particles, is selected to incorporate a metal or metal ions having an atomic number greater than 20 and of at least about 40. A synergistic effect may be achieved by employing at least one of a cytostatic drug therapy and a genetically based therapy to treat the tumor, in combination with the locally enhanced radiation therapy.

61 Claims, 1 Drawing Sheet

6,001,054

METHOD AND APPARATUS FOR DIFFERENTIAL ENERGY APPLICATION FOR LOCAL DOSE ENHANCEMENT OF IONIZING RADIATION

BACKGROUND OF THE INVENTION

The present invention relates to methods and apparatus for delivering effective dosages of radiation therapy to selected sites in the body to inhibit proliferation of tissue, and particularly to selective localized enhancement of radiation dosage using low level sources.

As the average age of the population of the industrialized countries increases, and with it, the prolongation of exposure to environmental hazards, a corresponding increase is seen in the risk of cancer, and in the number of people with neoplasias and tumors. Radiation therapies which have heretofore been applied to treat tumors have had little differential effect. That is, to the extent that the dosage of radiation is effective to destroy or at least alter the growth rate of the tumor, it is also effective to place considerable stress and injury upon surrounding healthy or non-diseased tissue.

Interventional cardiology and interventional angiology have enjoyed increasing popularity in recent years for treating various vascular and duct disorders involving lesions. The numbers of implantations of prostheses for such treatment, and new applications that are under consideration, are growing rapidly with time, but new problems have arisen as well. For example, in treating carotid artery stenosis by a minimally invasive interventional procedure which removes or reduces the thickness of plaque on the inner lining of the vessel, the initial success of opening the lumen is often followed within only weeks by restenosis which is attributable to a neointimal hyperplasia reaction to the original procedure. This occurs in a significant percentage of the population of patients subjected to such a procedure, which appears to range from 20% to 35%, depending on the lesion type and length, the vessel size, and underlying basic conditions of the patient, such as diabetes mellitus.

Among solutions that have been proposed to inhibit, alleviate or prevent restenosis are the use of a radioactive stent which would serve to lessen or eliminate the healing response of hyperplasia, and/or coating of the stent with a biodegradable carrier which would disintegrate over time when the stent is deployed in a blood vessel, to release anti-proliferative substances incorporated therein. These procedures, however, would necessarily be used for all angioplasty patients because it cannot presently be determined which patients will be among the approximately 20% to 35% who will suffer restenosis as a result of proliferation of tissue in the healing response. Thus, about 65% to 80% of angioplasty patients who receive a radioactive stent, for example, would not have actually developed a restenosis, and would not have had to be subjected to treatment for an adverse reaction to the procedure.

It is a principal aim of the present invention to provide a method and means of treating angioplasty patients and other patients who are subjected to tissue trauma in a body vessel, duct, tract or other passageway in the body sought to be relieved from an obstruction, that actually leads to an acute restenosis, without need to perform a subsequent or even concurrent prophylactic and possibly injurious treatment on every patient who receives an angioplasty or related procedure, a large percentage of which will not experience the restenosis.

Additionally, it has been found that especially with the increasing number of prosthetic implants being performed in surgery, orthopedics and dental medicine, a certain percentage of the patients will suffer from an enhanced foreign body reaction. For example, when a hip prosthesis is implanted the patient may experience a reaction of the surrounding tissue which can compromise the healing process and the firmness or retention of the implant. This same problem is encountered in a measurable percentage of patients who receive dental and other surgical implants.

Accordingly, a related aim of the invention is to provide a localized form of treatment that allows such foreign body reaction to be selectively addressed in only those patients who suffer the problem, and to deliver the treatment in a way that is effective without any significant potential for harm to adjoining or nearby tissue that may be exposed to the treatment.

In efforts to treat localized solid tumors in the body, with an ever-increasing number of procedures owing to an increasing rate of tumors in the bronchial system and in the abdominal intestines, surgical removal may not be a viable option especially if the malignancy has metastasized and spread to other portions of the body. In many instances, the tumor may cause blockage of a duct or passage. A stent may be implanted to keep the lumen open, such as in the lumen of a bronchial passage or of a duct in the gall bladder, but experience has shown that tumor growth can again cause the lumen to become occluded. A localized action to slow or inhibit tumor growth would be desirable to prevent or reduce such occlusion.

It is known that the capacity to inhibit solid tumor growth and even destroy the tumor, by means of ionizing radiation treatment, depends on the types of cells involved and their sensitivity to radiation. Each individual tissue has its own sensitivity to radiation. Exposure of the skin to mild radiation can produce a skin burn, whereas exposure to larger doses can produce a skin necrosis. In the case of treatment of a tumor in the body, it is desirable to use a higher level of radiation, sufficient to produce a radiation dose at or near the tumor site in a range upward of 20 Gray (Gy). Delivery of a dosage in the range from about 20 to 200 Gy to the tumor site can be effective to induce necroses or apoptosis in the tumor and inhibit further growth, but typically the externally generated radiation (usually a beam of X-rays or accelerated electrons using a collimator, rather than a mass of radioactive material as had been the technique in the earliest treatment) is directed toward a tumor deep below the skin. Only rarely is the tumor at or directly beneath the skin, the much more frequent situation being that considerable healthy tissue lies between the skin and the tumor site. To deliver a dose of radiation adequate to have a desired effect on the tumor (albeit that it may not be completely successful, even over several sessions of the radiation treatment) it is necessary to accept the likelihood that intervening healthy tissue may be severely harmed by the impinging radiation. For example, in the case of liver carcinoma or a metastasis in the liver that requires treatment, it is necessary to penetrate not only the skin, fatty tissue and bowel that overlie the site of the metastasis with the radiation, but also the normal and still functional liver tissue in its path.

It is therefore another important aim of the present invention to provide a method and means for locally enhancing the therapeutic effects of radiation treatment of relatively deep body tumors, in a way that will allow effective treatment of the tumor with considerably lower doses of radiation than would otherwise be required, so that non-diseased tissue is subjected to substantially less harmful effect.

Still another important objective of the invention is to utilize locally enhanced radiation therapy to make a tumor more susceptible to attack and eradication by other forms of tumor treatment, such as cytostatic therapy, chemotherapy, genetically engineered drug therapy, or cancer gene therapy. In the latter treatment as proposed, genes which have been altered to render them damaged or defective as a possible result of cigarette smoking, excessive exposure to sunlight or toxic chemicals, for example, are repaired or replaced by inserting other genes carried by modified viruses into the cancer cells.

SUMMARY OF THE INVENTION

Exposing human tissue to ionizing radiation is effective to reduce cell proliferation if the dosage delivered to the locality (vicinity) of the tissue selected to be treated is sufficiently high (e.g., at or above 20 Gy) to produce an immediate necrosis (i.e., occurrence of immediate cell death) or to induce an apoptotic stage (i.e., occurrence of programmed cell death, immediately or within the next cycle or future generations of cell cycles). The result is either a total or partial reduction in the number of proliferating cells. As observed in the background section above, the problem is that while delivery of a high dosage of radiation in the range from 20 to 200 Gy is desirable to treat a tumor or to alleviate hyperplasia, it can be a deleterious and possibly lethal dosage also to surrounding healthy tissue.

An X-ray source can be implemented by known techniques to generate a beam of radiation having an energy content in a range from 10 KeV to 400 MeV. Current radiation therapy typically employs radiation ranging from 500 KeV to 42 MeV. Use of radiation levels below 500 KeV has been limited primarily to surface therapy, as being insufficient to treat deep tumors or deep sites of potential proliferation of tissue. If such a radiation beam contacts a metal surface, the dosage of X-ray radiation is amplified by a factor of from 1.8 to 2.5 at the metal surface owing to backscatter radiation, which is attributable to a photomultiplier effect. Heretofore, this amplification by an approximate factor of two has not been found useful for differentiation of the applied energy, with a range of penetration of the backscatter radiation up to about one centimeter (cm) from the metal surface.

Research conducted by the applicants herein has shown, however, that an interesting phenomenon occurs at the metallic surface with radiation energy levels below about 400 KeV. In fact, the applicants have found that for radiation below this level, the amplification factor resulting from backscatter from the metallic surface is inversely proportional to the applied voltage. The lower the KeV level of the radiation, the higher the amplification factor, up to an apparent maximum factor of about 200× for a radiation level of 40 KeV. The 40 KeV level at which this maximum amplification from backscatter occurs, has itself previously been considered to be relatively low or "soft". Also, the effective penetration of this secondary backscatter radiation appears to lie in a range from about 20 micrometers ($\mu$m), or microns, to about 100 $\mu$m from the metallic surface, and evidences an inverse correlation with the voltage level of the impinging radiation. The applicants have also found that the range of the backscatter radiation depends on the physical characteristics of the metal, and in particular, on the atomic number of the metal, expressed as Z, in the periodic table of elements.

Among the heavy metals, which are preferred in that they have the higher atomic numbers, it appears that an optimum or maximum for the backscatter radiation effect occurs at Z=60, which corresponds to the element iodine. Below and above this atomic number, a reduction in backscatter amplification takes place. Nevertheless, for noble metals such as gold, platinum and iridium, which have Z numbers up to about 80, the amplification factor—although reduced from the maximum—is found to lie at about 100, which is still quite considerable when compared to the relatively low level of radiation which is unaided by the presence of the metallic surface at the interface of the tissue to be treated.

The amplification effect enables a closely controlled local dosage enhancement of impinging radiation for therapeutic applications, especially those involving tissue proliferation which is found in the mechanism that produces a benign but problematic restenosis and a malignant lethal tumor. By way of example, as was noted earlier herein, a radiation dosage of 20 Gy has been found to be effective to inhibit a proliferation of smooth muscle cells in a carotid artery that has undergone angioplasty. If left untreated after the angioplasty, the resulting restenosis could produce a complete blockage of the artery. If external beam radiation is employed to deliver the desired dose, there remains the problem of also irradiating healthy tissue with the relatively high intensity beam used to reach the site in the carotid artery to be treated. A potential solution would be to irradiate the arterial wall at the designated site from within the artery itself, as has been proposed, for example, by implanting a radioactive stent at that site. The stent then serves the dual purpose of delivering radiation—such as from a Beta source of limited penetration and relatively short half life—and of buttressing the arterial wall against collapse.

According to an important aspect of the present invention, a desirable alternative is to implant a metallic stent which has not been made radioactive, to maintain the lumen of the carotid artery (or other vessel, duct, tract or passageway of interest in the body) open to allow adequate flow of blood (or passage of other fluid or solid materials normally permitted within the respective lumen) therethrough. Then, if it is subsequently found that restenotic processes are taking place following the therapy which required the stent to be implanted in the first place, beam X-ray radiation of relatively low intensity can be used to deliver a dosage of, say, only 0.20 Gy to tissue contacting the stent surface. And, if the implanted stent has a noble metal coating, such as gold, which will allow even greater local enhancement by virtue of the amplification effect (about 100, as noted above) than with a low Z metal, then an amplified dosage of about 20 Gy is delivered in the immediate vicinity of the stent surface. The restenotic processes are quite localized themselves, and since the thickness of a neointimal proliferation is in a range from about 100 to 1000 $\mu$m, the focused and very distinct backscatter radiation attributable to the presence of the metallic surface—here, the stent, and particularly if the stent's surface is a metal of appropriate atomic number (Z) to provide a high amplification—can deliver dosages in the vicinity of the implant which are sufficient to inhibit proliferation and thereby, restenosis, or further tumor growth.

Three remarkable results take place with such a solution. One is that the amplification effect of the metal surface enables relatively high dosages to be delivered at precise locations with relatively low radiation or energy levels in the impinging beam. Another is that the intensity of the radiation that penetrates the healthy tissue between the skin of the patient and the tissue at the site to be treated, along the inner lining of the artery, is sufficiently low level to preclude a likelihood of damage to the healthy tissue. And the third is that the capability to locally enhance the external beam radiation at the selected site makes it unnecessary to implant a radioactive stent, which, although the radioactive source material may be of short half life and limited penetration, can have a damaging effect on some otherwise healthy tissue in the vicinity of the treatment site.

Yet another benefit of this treatment provided by the present invention is that it is not necessary to treat every angioplasty patient as though he or she will suffer restenosis at the site of the original treatment. This means that every patient need not be implanted with a radioactive stent or a stent coated with a biodegradable carrier from which an antiproliferative substance, drug or agent is released, for example, or treated by means of an invasive technique other than or in addition to stenting at the same time as the angioplasty is performed or at some later time. Instead, the site can be examined by X-ray fluoroscopy during scheduled visits by the patient to the attending physician. The restenotic processes are acute but typically of sufficiently long duration that if the patient is among the 20 to 35% predisposed to such a condition, examinations within the two to six-week period following the original procedure will reveal the condition as being present. At that time, the appropriate radiation dosage may be delivered from an external source using the amplification effect of the already implanted stent.

Another application of the techniques and apparatus of the invention is to treat patients who have undergone an angioplasty or similar procedure with the localized dosage-enhanced applications of backscatter radiation from a metallic surface implant as a preventive measure, to avoid or reduce the likelihood that a restenotic lesion will develop Although this would not be a selective process because it has not yet been determined how to identify the patients who will suffer a restenosis from among the entire population of angioplasty patients, nevertheless, the invention allows the use of sufficiently low levels of radiation to reduce the likelihood of harm to healthy tissue. And, since the irradiation technique is performed external to the patient, the individual is at considerably less risk than is the case with existing invasive procedures and which typically have longer lasting effects.

As another application, the invention is suitable to treat solid tumors effectively, toward destroying the tumor or at least stabilizing the patient to prevent or inhibit further growth or spread of the malignancy. Additionally or alternatively, treatment according to the invention is intended to make the tumor more susceptible and sensitive to other forms of cancer treatment. Such other forms of treatment may, for example, consist of the conventional systemic or local application of cytostatic drugs—one or several in combination such as cisplatin, 5 fluorouracil, taxol, tamoxifen, vincristin, and so forth—or newer treatment forms such as cancer gene therapy and genetically engineered drug therapy. A summary of the current status of the latter therapeutic approaches is presented, for example, in the May 6, 1998 edition of the Wall Street Journal, at pages A1 and A12, and incorporated by reference herein.

In cases where the tumor lies in, about or adjacent to a tract of the body, a stent may be implanted by the usual procedure, that is, inserted into the tract on a stent delivery system, e.g., a balloon catheter, advanced to the designated site, and deployed by expanding the stent diameter to engage the inner wall of the lumen. The irradiation is then performed in the same basic manner as is done to treat actual or potential restenosis, although the dosage to be delivered to a tumor may far exceed that used for treating restenosis. Here again, the invention provides the advantage of localized enhancement of the dosage by means of the amplification effect through backscatter radiation from the metallic surface.

But where the tumor is in a location where implantation of a stent is either difficult or not practicable, such as in the gastrointestinal organs or in the bronchial system, the metal surface may be provided by use of a metallic contrast dye. For example, a tumor of the colon may be treated by first delivering a contrast dye such as barium sulfate into the colon. Barium is a heavy metal which is not absorbed by the body and which will stay within the lumen of the bowels. The contrast dye may be preferentially disposed to keep the barium at the inner lining of the colon and at a very precise designated site by advancing a balloon of a catheter to the site, and then inflating the a balloon with a fluid to compress the contrast dye against the lining. This then provides the metallic surface against which the externally generated X-ray radiation beam is directed for amplified backscatter radiation in a locally enhanced dosage which has been calculated to provide the desired radiation therapy.

According to another aspect of the invention, a heavy metal such as an iodine contrast dye is applied to an organ or other body region invaded by the tumor, by means of a bolus application or a continuous flow with a perfusor for the time interval during which the organ is to be irradiated. Following perfusion of the tumor with heavy metal ions in this way, a differential local dose enhancement of up to 200 amplification of local radiation is achieved, with consequent desired reduction of unwanted side effects to adjacent healthy tissue. By combining the local irradiation with prolonged action of cytostatic drugs applied locally to the tumor, the effects of both the radiation and the cytostatic drugs are amplified by a synergistic effect.

In instances where a continuous flow of contrast dye may not be suitable, such as for organs or other parts of the organism having a very high metabolic turn-over rate where the contrast medium will not remain in place for a sufficient time interval, an embolization type of technique is preferred to implement the principles of the present invention for treatment of tumors. Toward that end, an embolization agent or substance is utilized to significantly reduce blood flow in designated vessels, those vessels being the arteries and veins which provide the blood supply to the tumor. It is common practice to identify such tumor arteries and veins by catheter placement and use of contrast dye. Once the vessels are identified, proliferation inhibitors are applied to the affected organ or region of the body through these vessels. The proliferation inhibitors are substances in the form of chemical drugs such as tamoxifen, taxol, rubimycin and other cytostatic agents appropriate for the individual type of cell. More prolonged local action may be achieved by applying liposomes incorporating the cytostatic drugs locally to the tumor.

According to this aspect, the present invention employs an embolization agent incorporated in microspheres. Microspheres, which consist of small particles having a composition of albumin and other small proteins, and which range in size (diameter) from 5 to 100 $\mu$m, are known and conventionally used in medicine. For purposes of the present invention, metallic substances such as iodine or even gold are incorporated into the microspheres by loading the microspheres with the metal ions. The microspheres are then introduced into the vascular system, and, depending on their physical characteristics, will be absorbed in tissue at a vessel site of corresponding diameter. That is, microspheres of 5 $\mu$m diameter, for example, may pass through the capillary bed and return into the vascular system, whereas microspheres that exceed a capillary size of about 5 $\mu$m to 7 $\mu$m will be absorbed locally. Thus, the smaller the microspheres that will not pass the capillary bed, the more homogeneous will be their local distribution.

If microspheres having a size on the order of 10 μm are used, a very tight and homogeneous penetration of a tumor can be achieved according to the matching of the size of the microspheres to the small vessels. Increasing the size of the microspheres introduced into the vascular system will cause more of them to be absorbed and blocked in the small arteries (arterioles) of a size in a range from 10 to 40 μm. It will therefore be seen that the size and metallic surface (according to its atomic number Z) of the microspheres can be taken into account, together with the energy of the radiation source expressed in KeV (thousands of electron volts), and with the understanding that the larger the size of the microspheres and the greater the distance between them the higher the energy required to increase the range of radiation, to arrive at a set of values for each of these parameters at which an optimum amplification of radiation impinging on the local distribution of the microspheres is achieved.

The external radiation beam is directed toward the target site under treatment, to which the microspheres have been applied or at which at least a local penetration has taken place. By using fluoroscopic identification of the target lesion site, a very narrow, centered radiation beam having an energy intensity ranging from 40 to 400 KeV may be applied. By virtue of the nature of the amplification and the short range of penetration of the backscatter radiation arising therefrom, although an adequate radiation dosage is attained for purposes of suppressing proliferation of tissue, the dosage absorbed by tissue at a location outside the local enhancement region is minimal and considerably less than what is required to have an adverse effect on healthy tissue.

BRIEF DESCRIPTION OF THE DRAWINGS

The above and other aims, objectives, aspects, features and attendant advantages of the invention will be further understood from the following detailed description of the best mode presently contemplated for practicing the invention, by reference to presently preferred embodiments and methods, taken in conjunction with the accompanying drawings, in which:

FIG. 1 is an exaggerated cross-sectional view of a blood vessel or other body duct or passageway illustrated as being treated by the method of the invention;

FIG. 2 is a cross-sectional view of a body duct with a tumor treated using a contrast dye and a balloon catheter to properly position the metal ions therein;

FIG. 3 is a cross-sectional view of a deep body tumor through which a catheter or needle is inserted to provide the desired metallic surface for impinging radiation; and FIG. 4 is a cross-sectional view of a deep body tumor in which a contrast dye is injected into the tumor by means of a bolus or through continuous flow.

DETAILED DESCRIPTION OF THE PREFERRED EMBODIMENTS AND METHODS

From the preceding summary it will be understood that, according to the invention, human tissue is exposed to a dosage of radiation which is effective to inhibit or substantially reduce cell proliferation, by an intentional positioning of metal or a metallic surface in the locality (vicinity) of the tissue to which the lethal dosage (or substantially so) is to be delivered, i.e., the tissue which has been selected to be treated, and then directing a beam of radiation to impinge on the metallic surface to achieve an amplifying effect. In addition, the invention contemplates that the energy content of the incident beam should be in a predetermined range (i.e., level or intensity) ordinarily considered to be much too low for such treatment, but which in fact can produce an optimum amplification—or nearly so—from the enhancement reaction with the metal surface, and particularly if the metal is selected according to its atomic number to provide considerable further enhancement. By virtue of the relatively low range (i.e., distance) of penetration of the radiation of significant intensity that backscatters from the metallic surface, albeit somewhat increased by the atomic number selection, this assures that an effective dosage is delivered to the designated tissue adjacent the metallic surface, and that healthy tissue located only a slight distance from the tissue to be treated will be virtually unscathed by the radiation. And since the intensity of the radiation in the beam is purposely set to be low to achieve greater amplification, neither the incident nor reflected radiation can deliver a harmful dosage to the healthy tissue.

In FIG. 1, an X-ray source 10 of conventional construction is capable of generating a beam 12 of X-ray radiation with an energy content in a range from 10 KeV to 400 KeV—well below the range currently employed for radiation therapy to treat tumors within the body (the latter typically being from 500 KeV to 42 MeV). The energy content of beam 12 is generally deemed to be inadequate to treat more than surface tissue, certainly incapable of effective treatment of malignant tumors lying rather deep within the body or possibly of sites such as in the vascular system where trauma may lead to cellular tissue proliferation which, although benign, can produce harmful blockage through restenosis of a vessel. On the other hand, a radiation source of higher intensity to be used for such purposes would deliver undesirable radiation dosage levels to intervening normal tissue.

By way of example, if a patient has undergone an angioplasty procedure to relieve blockage of a coronary artery, there may be a predisposition toward an acute reocclusion as a result of cell proliferation at the treated site from the procedure itself. According to one important aspect of the invention, it is not necessary to treat every patient for this possibility, as has been proposed with other techniques, even though less than half the patient population will suffer this effect. Rather, if it is found upon subsequent examination of the patient in a period from a few days to up to about six weeks after the procedure, that such proliferation is occurring, then treatment may be administered. The invention takes advantage of the fact that it is now customary to implant a metal stent at the site where the angioplasty was performed. This is done immediately after the first procedure, to buttress the vessel wall against collapse as well as to avoid further obstruction. It has been proposed that the inner lining of the artery be irradiated from within before stenting, or that the stent be made radioactive before implantation, to inhibit the possibility of hyperplasia at the angioplasty site. Since no reliable method has been advanced to determine which patient will experience the hyperplasia and which patient will not, such treatment must be applied indiscriminately to every patient. This adds significantly to the cost of overall treatment as well as to the possibility of unwanted side effects.

In FIG. 1, a metal stent 15 is illustrated (in a highly exaggerated showing) as having been implanted in a blood vessel 17 such as a coronary artery which is relatively deep below the skin 18 of the patient. In the method of the invention, if the patient is found to be experiencing hyperplasia at the angioplasty site, after patient preparation and location in a safe room for the procedure, a low intensity beam (e.g., under 400 KeV) 12 of X-ray radiation is narrowly directed onto the affected artery 17 and is thereby incident upon the surface of the metal stent 15. Backscatter radiation 20 which results from the presence of the metal surface is amplified by at least approximately a factor of 10 as a consequence of photo-multiplier effect, with a range of penetration of up to about several mm toward the vessel wall from the point of contact between its inner lining and the stent surface. The radiation dosage delivered in those circumstances, however, may be inadequate to provide the desired proliferation-preventive effect.

To further assure that the desired salutary effect is achieved, two steps are taken. For one thing (not necessarily the first step), the energy level of the incident radiation is maintained below about 400 KeV, and most preferably at or near a level of 40 KeV, where amplification of up to about 200× is theoretically achievable with an effective range of penetration of about 20 to 100 $\mu$m from the metallic surface. The magnitude of the amplification drops off rapidly with even very slight increases in distance from the point of incidence.

For another thing (not necessarily the second step, and indeed, a step that would be taken ordinarily before the patient is subjected to beam radiation), the particular metal of which the stent is composed, and most especially its metal surface, is selected to have an atomic number (Z) at or near 60, at which the optimum amplification of about 200× appears to be achievable. This corresponds closely to the atomic number for the element iodine, and for metals with lower and higher atomic numbers, a reduction in the backscatter radiation amplification occurs. According to the invention, the surface of the metal object (whether it be a stent or other object) on which the radiation will be incident, such as the outer surface 22 of stent 15 is coated with a thin layer (which need only be on the order of a few $\mu$m) of a noble metal such as gold, platinum, or iridium or alloys thereof The noble metals approximate Z=80, which provides an amplification factor of about 100× for the backscatter radiation.

By virtue of these two steps, coupled with the initial use of a metal surface on which the radiation is to be directed, a differential, closely controlled local dosage enhancement is achieved for therapeutic applications, and specifically for treatment in instances where uncontrolled abnormal proliferation of tissue is occurring. Delivery of an effective radiation dosage of 20 Gy at the site of the tissue to be treated, to inhibit proliferation of smooth muscle cells in the lining of artery 17, for example, may thus be obtained from external beam radiation with energy content suitable for a dosage at that site of only 0.20 Gy, absent the 100× amplification. For the neointimal proliferation that occurs with restenosis of a blood vessel or other body duct or passageway, the depth of the tissue requiring treatment is approximately 200 to 1000 $\mu$m, and effective dosage is achievable within that range from the method of the invention.

To assure adequate and effective treatment of the entire site of the angioplasty, the beam radiation is delivered in incremental arcs in the overall circumference of the artery length encompassed by the site. This requires that the patient or the radiation source undergo periodic rotation timed to deliver the designated dosage within each arc. However, since the time required for such delivery is very short, and the level of radiation to which the body is subjected is very low, the overall treatment is performed quickly, without measurable harm to the body and little discomfort to the patient. Although the treatment is preferably limited to those patients who are found to experience the hyperplasia after the original procedure, it is within the scope of the invention to apply its techniques and benefits as a prophylactic or preventive measure for all patients who undergo the original procedure.

The invention is also applicable to treatment of solid tumors. In instances in which the tumor is in or partially or fully surrounds a natural duct of the body, such as the gastrointestinal system, the colon, the ductus hepaticus, ductus cysticus or ductus choledochus which connect the liver, gall bladder and pancreas to the intestines, or the bronchial system, a stent likewise may be implanted in the duct, either temporarily or permanently, for use in conjunction with the method of the invention as has been described with reference to FIG. 1. Preferably, however, in those instances and also where the tumor is located away from a natural duct or tract, a metallic contrast dye is employed to provide the metal surface.

Figure 2:
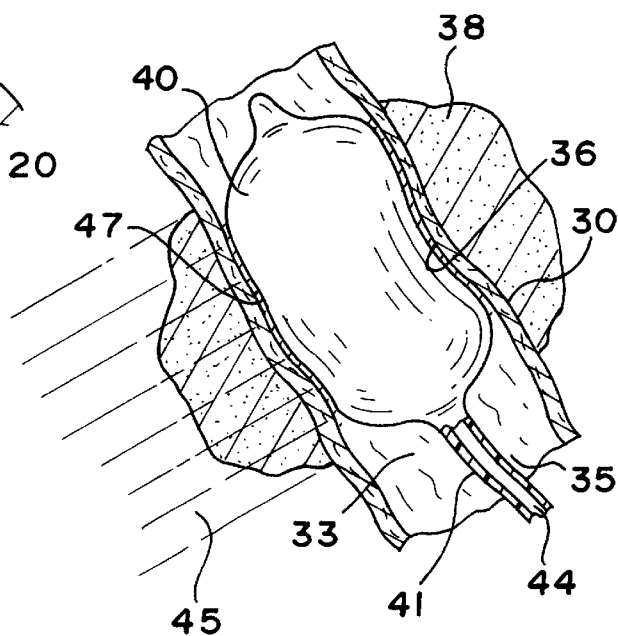

Referring to the example of FIG. 2, for a tumor of the colon 30, a contrast dye 33 of barium sulfate is injected into the lumen 35 of the colon, with the advantages that barium is not absorbed by the body and thus readily confined to the bowels. The contrast dye is contained to maintain barium in contact with the inner lining 36 of the colon in the region of the tumor 38 (here shown outside the colon for greater clarity in the accompanying description, although the tumor may instead or additionally reside within the colon) by means of a balloon 40 of a catheter 41 which has been advanced to the tumor site. Once in the proper location, which is viewed by fluoroscope or by use of an endoscope on the catheter, the balloon is inflated by injecting fluid through an inflation lumen 44 of catheter 41, to compress the contrast dye 33 against the lining 36 in that region. An externally generated beam 45 of radiation is then directed onto the tumor and to impinge upon the metallic surface 47 provided by the barium contrast dye layer trapped between the inner lining of the colon and the membrane of the balloon. The prescribed locally enhanced dosage of amplified backscatter radiation is delivered in the region of the tumor as a therapy to destroy the tumor.

Figure 3:
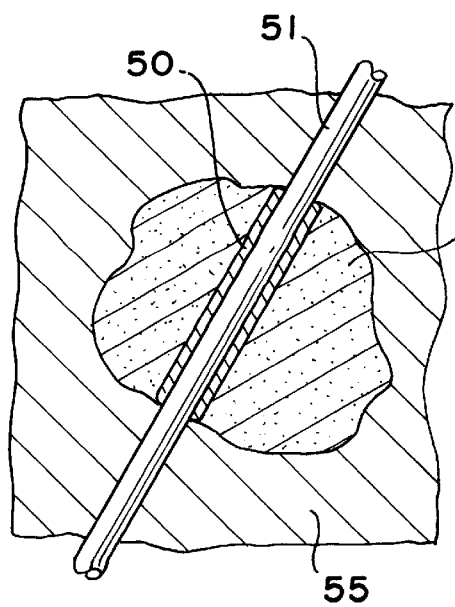

It is also possible, where the tumor is not otherwise accessible, to implant a catheter or even several catheters into the surrounding tissue and through the tumor, using catheters which have been clad with a metal selected according to the principles of the invention along an appropriate portion of the length thereof, as shown in FIG. 3. In the Figure the thickness of the metal cladding or coating 50 on the catheter 51 is exaggerated for the sake of clarity. The length of catheter to be accommodated by the coating, and its location along the length of the catheter 51 are readily determined from an X-ray or MRI (magnetic resonance imaging) scan of the tumor 53 and its location in the patient's body 55. Instead of catheters, needles which may or may not be associated with syringes, may be used to penetrate the tumor and provide the desired metallic surface(s).

Figure 4:
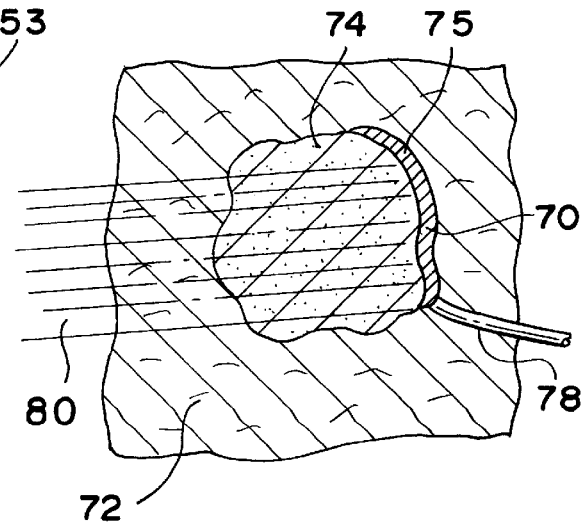

Alternatively, as illustrated in FIG. 4, an iodine or other heavy metal contrast dye 70 is injected in or applied to an organ or other body region 72 invaded by a tumor 74. The contrast dye is relatively confined to a desired portion 75 at the periphery of the tumor location to be treated, by use of a bolus or by continuous flow using a perfusor 78, over a relatively brief period of time during which the tumor is to be irradiated. An externally generated beam of radiation 80 is directed onto the tumor from a direction in which it will be incident on the heavy metal ion surface for backscatter of radiation so that a differential local dose enhancement of desired magnitude is delivered into the tumor. A synergistic effect may be achieved by combining the irradiation with a prolonged action of cytostatic drugs which are applied locally to the tumor, or by the aforementioned gene therapy approaches.

It is also within the contemplation of the present invention that a radioactive source such as a radioactive isotope of iodine (e.g., $^{131}$I or $^{125}$I) is applied to tissue such as thyroid tissue in which a malignant tumor is present, to be absorbed by and accumulate therein, and, additionally, a beam of radiation generated external to the body as previously described herein is directed onto the tumor or affected tissue whereby to achieve backscatter and dosage amplification from the presence of the iodine, to enhance the therapeutic effect of both the radioactive iodine and the external beam radiation.

For organs or other body regions that have a very high metabolic turn-over rate, an embolization agent or substance may be injected to reduce blood flow in designated arteries and veins that supply blood to the tumor. The desire is that, without this source of blood supply, the tumor will whither and die. The blood vessels of interest are identified by catheter placement and use of contrast dye, and are then used for application of proliferation inhibitors, such as tamoxifen, taxol, rubimycin and other cytostatic agents, to the affected organ or region of the body. Alternatively, liposomes incorporating the cytostatic drugs may be applied locally to the tumor by selective injection into the regional blood vessel supply, for a more prolonged local action.

Preferably, the embolization agent is incorporated in small particles, or microspheres, of from about 5 to 100 $\mu$m in diameter composed of albumin and other small proteins. The microspheres, with metallic substances which may include iodine, gold or other elements incorporated therein, are inserted or injected into the arterial system. The small particles will initially flow with the vascular system into the tissue or tumor of interest, but will not cross from the arterial blood supply side to the venous side since they are trapped in the capillary bed. That is, they may not pass through the capillary bed and return, if of larger diameter than the capillaries of 5 to 10 $\mu$m, and are absorbed locally in tissue of corresponding diameter. The desire is to obtain a homogeneous local distribution of microspheres in the arterioles of the tumor, which is achieved by using microspheres of about 10 to 40 $\mu$m in diameter, and this will allow them to be absorbed and to block these small arteries. The combined metallic surface provided by the microspheres also serves to enable differential local enhancement of the dosage of radiation to be obtained from an external narrow radiation beam preferably with an energy intensity ranging from 40 to 400 KeV, directed onto the tumor.

Although certain preferred embodiments and methods have been disclosed herein, it will be appreciated by those skilled in the art to which the invention pertains, from a consideration of the foregoing description, that variations and modifications may be made with respect to these examples without departing from the spirit and scope of the invention. Accordingly, it is intended that the invention shall be limited only by the appended claims and the rules and principles of applicable law.

What is claimed is:

1. A method of providing a differential therapeutic effect on a targeted lesion site within a human body, which comprises the steps of positioning a metallic surface within the body adjacent said lesion site, directing a beam of radiation of predetermined energy intensity less than about 400 KeV onto the lesion site to impinge on the metallic surface, whereby to achieve amplification of backscatter radiation from the metallic surface into the lesion site, to locally enhance the radiation dosage delivered to the lesion site to a level considerably exceeding the dosage which would be attributable to the intensity of the radiation beam alone if the metallic surface were not present.

2. The method of claim 1, wherein the lesion site is adjacent a substance-carrying vessel of the body having a lumen through which the substance moves, and said metallic surface is the surface of a metal material deployed in the vessel at said lesion site.

3. The method of claim 2, wherein said substance-carrying vessel is in the body's vascular system.

4. The method of claim 3, wherein said lesion site is a site in the lumen of a blood vessel at which a stenosis has been treated.

5. The method of claim 4, wherein said metal material is a stent.

6. The method of claim 5, wherein the surface of the stent is coated with a layer of a noble metal.

7. The method of claim 4, wherein said metal material is a catheter having a metal surface at the site at which the stenosis was treated.

8. The method of claim 7, further including the step of removing the catheter from the blood vessel after irradiating said site with the radiation beam.

9. The method of claim 4, wherein said metal material is a contrast dye that contains a metal substance.

10. The method of claim 2, wherein the radiation beam is an X-ray beam.

11. The method of claim 2, wherein the metallic surface has an atomic number of at least about 40.

12. The method of claim 2, wherein said substance-carrying vessel is a duct of the body.

13. The method of claim 12, wherein said lesion site is a site of a solid tumor adjacent said duct.

14. The method of claim 13, wherein said metal material is a stent.

15. The method of claim 14, wherein the surface of the stent is coated with a layer of a noble metal.

16. The method of claim 13, wherein said metal material is a catheter having a metal surface in the duct adjacent the site of the solid tumor.

17. The method of claim 16, further including the step of removing the catheter from the duct after irradiating said site with the radiation beam.

18. The method of claim 13, wherein said metal material is a contrast dye that contains a metal substance.

19. The method of claim 18, wherein the metal substance in the contrast dye is barium.

20. The method of claim 12, wherein the radiation beam is an X-ray beam.

21. The method of claim 12, wherein the metallic surface has an atomic number of at least about 40.

22. A system for providing a differential therapeutic effect on a targeted site of tissue to be treated within a human body to inhibit cell proliferation, comprising a metallic surface positioned within the body adjacent said tissue site, and a source of radiation for generating a beam of radiation having an energy content in a range from about 10 KeV to about 400 KeV to be selectively directed onto the tissue site to impinge on the metallic surface, whereby to achieve amplification of backscatter radiation from the metallic surface into the tissue site, to locally enhance the radiation dosage delivered to the tissue site to a level considerably exceeding the dosage attributable to the intensity of the radiation beam alone if the metallic surface were not present.

23. The system of claim 22, wherein the metallic surface is positioned at a tissue site adjacent to a substance-carrying vessel of the body having a lumen through which the substance moves, and said metallic surface is the surface of a metal material deployed in the vessel at said tissue site.

24. The system of claim 23, wherein said substance-carrying vessel is a part of the body's vascular system.

25. The system of claim 24, wherein said tissue site is a site in the lumen of a blood vessel at which a stenosis has been treated.

26. The system of claim 25, wherein said metal material is a stent.

27. The system of claim 26, wherein the surface of the stent is coated with a layer of a noble metal.

28. The system of claim 25, wherein said metal material is a catheter having a metal surface at the site at which the stenosis was treated.

29. The system of claim 25, wherein said metal material is a contrast dye that contains a metal substance.

30. The system of claim 23, wherein the source of radiation beam is an X-ray beam generator.

31. The system of claim 23, wherein the metallic surface has an atomic number of at least about 40.

32. The system of claim 23, wherein said substance-carrying vessel is a duct of the body.

33. The system of claim 32, wherein said tissue site is a site of a solid tumor adjacent said duct.

34. The system of claim 33, wherein said metal material is a stent.

35. The system of claim 34, wherein the surface of the stent is coated with a layer of a noble metal.

36. The system of claim 33, wherein said metal material is a catheter having a metal surface in the duct adjacent the site of the solid tumor.

37. The method of claim 33, wherein said metal material is a contrast dye that contains a metal substance.

38. The system of claim 37, wherein the metal substance in the contrast dye is barium.

39. The system of claim 33, wherein the source of radiation is an X-ray beam generator.

40. The system of claim 33, wherein the metallic surface has an atomic number of at least about 40.

41. A method for treating a site in a human body to inhibit abnormal proliferation of tissue at the site, which comprises the steps of employing within the body at the site a metal surface which generally conforms in shape to the shape of tissue to be treated at the site, and irradiating tissue at the site with ionizing radiation directed onto the metal surface from a point external thereto so as to obtain locally enhanced radiation therapy by an amplification of the radiation dosage delivered to tissue adjacent to the metal surface resulting from radiation backscattered from the metal surface.

42. The method of claim 41, including the step of selecting as the material for the metal surface a metal whose atomic number is greater than 20.

43. The method of claim 42, wherein the metal has an atomic number of at least about 40.

44. The method of claim 42, wherein the metal surface is solid.

45. The method of claim 42, wherein the metal surface is a composed of a multiplicity of spaced apart particles.

46. The method of claim 41, wherein the step of irradiating tissue is performed by directing a beam of ionizing radiation with an energy content selected to have a value in a range from about 10 KeV to about 400 KeV from a point external to the body toward the metal surface with the tissue to be treated intervening therebetween.

47. The method of claim 46, wherein the beam of ionizing radiation is selected to have an energy content of about 40 KeV.

48. The method of claim 46, including the step of selecting as the material for the metal surface a metal whose atomic number is greater than 20.

49. The method of claim 48, wherein the metal has an atomic number of at least about 40.

50. The method of claim 48, wherein the metal surface is solid.

51. The method of claim 48, wherein the metal surface is a composed of a multiplicity of spaced apart particles.

52. The method of claim 48, wherein said site is a portion of a body duct, and the metal surface comprises a stent deployed in said portion of the body duct.

53. The method of claim 48, wherein said site is a portion of a body duct, and further including the step of confining a contrast dye as the metal surface within said portion of the body duct.

54. The method of claim 53, wherein the step of confining the contrast dye within said portion of the body duct includes inserting a catheter within said portion of the duct and applying contrast dye as the metal surface between the lumen of the duct and the inner lining of the duct.

55. The method of claim 48, wherein said site is a solid tumor, and further including the step of applying the metal surface within the tumor.

56. The method of claim 55, wherein the step of applying the metal surface within the tumor is performed by injecting a contrast dye containing metal ions into the tumor.

57. The method of claim 55, wherein the step of applying the metal surface within the tumor is performed by injecting microspheres of less than 100 μm diameter containing metal ions into the tumor.

58. The method of claim 57, wherein the step of injecting microspheres into the tumor is performed by selective injection into blood vessels that supply blood to the tumor.

59. The method of claim 55, wherein the step of applying the metal surface within the tumor is performed by injecting radioactive iodine into the tumor, so that the therapeutic effects of both the radioactive iodine and the external radiation beam are enhanced by one another.

60. The method of claim 55, wherein the step of applying the metal surface within the tumor is performed by injecting an embolyzing substance into blood vessels that supply blood to the tumor.

61. The method of claim 55, including the step of achieving a synergistic effect by employing at least one of a cytostatic drug therapy or a genetically based therapy to treat the tumor, in combination with the locally enhanced radiation therapy.

* * * * *